US008839660B2

(12) United States Patent
Maier

(10) Patent No.: US 8,839,660 B2
(45) Date of Patent: Sep. 23, 2014

(54) LIQUID WATER PROTECTED IMPLEMENTATION OF A GAS QUALITY HYDROGEN SENSOR INTO A FUEL CELL EXHAUST SYSTEM

(75) Inventor: Oliver Maier, Worms (DE)

(73) Assignee: GM Global Technology Operations LLC, Detroit, MI (US)

( * ) Notice: Subject to any disclaimer, the term of this patent is extended or adjusted under 35 U.S.C. 154(b) by 502 days.

(21) Appl. No.: 13/294,498

(22) Filed: Nov. 11, 2011

(65) Prior Publication Data

US 2013/0122385 A1    May 16, 2013

(51) Int. Cl.
| | | |
|---|---|---|
| G01N 7/00 | (2006.01) | |
| H01M 8/06 | (2006.01) | |
| H01M 8/04 | (2006.01) | |
| G01N 33/00 | (2006.01) | |
| H01M 8/10 | (2006.01) | |

(52) U.S. Cl.
CPC ......... *H01M 8/04462* (2013.01); *G01N 33/005* (2013.01); *Y02E 60/50* (2013.01); *H01M 2008/1095* (2013.01)
USPC .......................................... 73/31.07; 429/414

(58) Field of Classification Search
CPC ..................... H01M 8/04194; H01M 8/04514; H01M 8/04522; H01M 8/04798; H01M 8/04843
USPC ...................... 73/31.07, 28.04; 429/413, 414
See application file for complete search history.

(56) References Cited

U.S. PATENT DOCUMENTS

| | | | | |
|---|---|---|---|---|
| 8,187,756 | B2 * | 5/2012 | Fujita et al. | 429/410 |
| 8,266,945 | B2 * | 9/2012 | Hartshorne | 73/28.04 |
| 2004/0101721 | A1 * | 5/2004 | Yoshida et al. | 429/20 |
| 2004/0229098 | A1 * | 11/2004 | Fujita | 429/25 |
| 2010/0304233 | A1 * | 12/2010 | Bhatti et al. | 429/413 |
| 2011/0174052 | A1 | 7/2011 | Kuebel | |

\* cited by examiner

*Primary Examiner* — Hezron E Williams
*Assistant Examiner* — Nathaniel Kolb
(74) *Attorney, Agent, or Firm* — Fraser Clemens Martin & Miller LLC; J. Douglas Miller

(57) ABSTRACT

A hydrogen sensor assembly is disclosed. A sensor is disposed within a slotted sleeve and a spiral shaped sensor housing surrounds the sensor within the sleeve. The spiral shape applies a centrifugal force to the fluid stream. This results in separation of liquid water from the fluid stream. The sleeve forms an internal inner perimeter of the spiral housing. The sensor housing includes a first opening to facilitate a fluid communication between the sensing element and a fluid stream through the slotted sleeve.

14 Claims, 1 Drawing Sheet

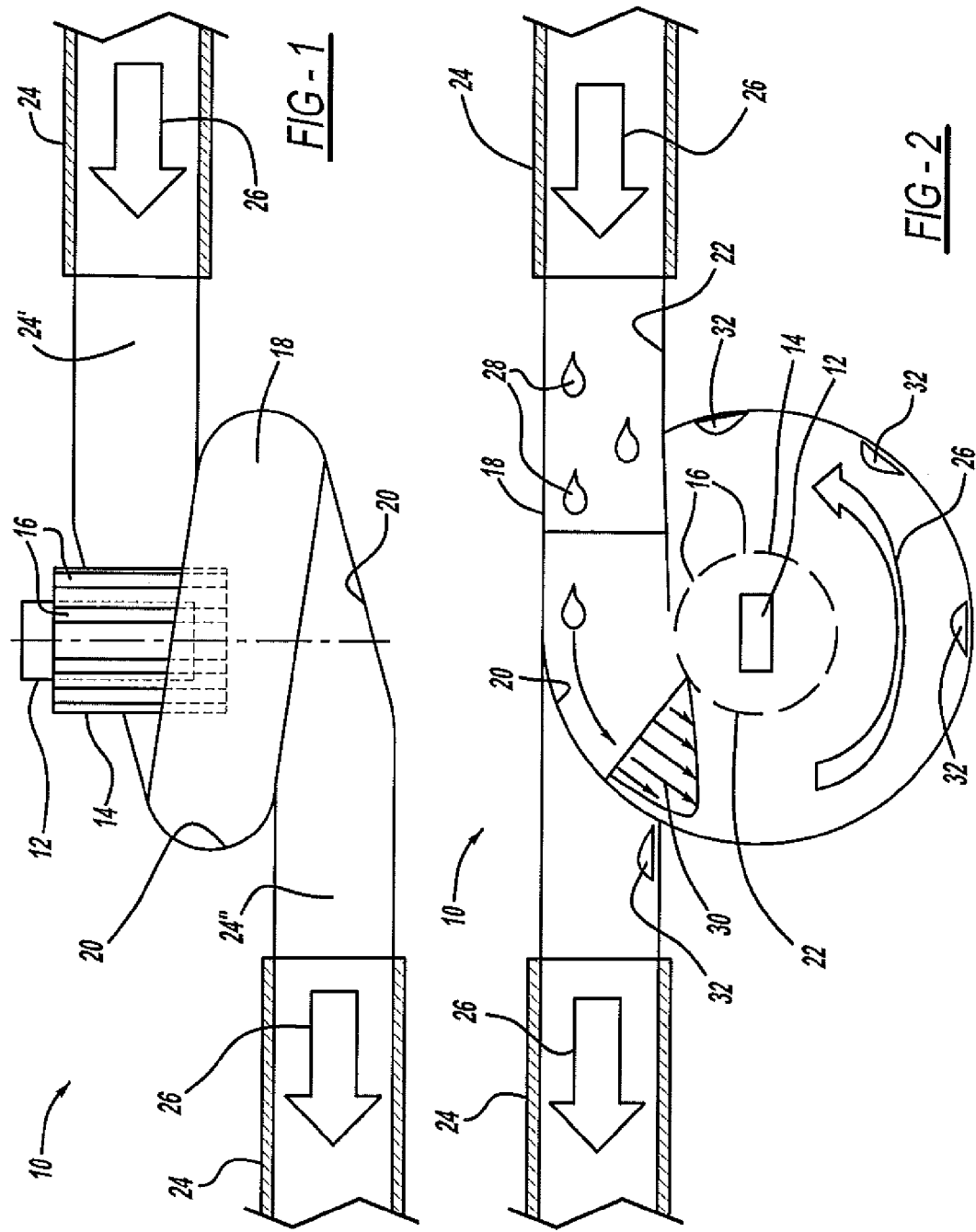

LIQUID WATER PROTECTED IMPLEMENTATION OF A GAS QUALITY HYDROGEN SENSOR INTO A FUEL CELL EXHAUST SYSTEM

FIELD OF THE INVENTION

The invention relates to fuel cell systems. More particularly, the invention relates to a hydrogen sensor assembly for measuring a concentration of hydrogen in a fuel cell exhaust stream.

BACKGROUND OF THE INVENTION

Electrochemical fuel cells are generally known in the art and convert fuel and an oxidant to electricity. One such fuel cell is a solid polymer electrochemical cell and includes a plurality of membrane electrode assemblies (MEA), each of which includes an ion exchange membrane or other electrolyte disposed between an anode and cathode. The MEA may include a catalyst or other catalytic material at each interface between the ion exchange membrane and the anode to induce a desired electrochemical reaction. The electrodes are electrically coupled to provide a circuit for conducting electrons between the anodes and the cathodes through an external circuit.

In a hydrogen powered fuel cell, hydrogen and air are supplied to electrodes on either side of the ion exchange membrane. Hydrogen is typically supplied to the anode where the catalyst promotes a separation into protons and electrons that are conducted through the external circuit. On the opposing side of the membrane, air is provided to the cathode where oxygen in the air reacts with the protons passing through the ion exchange membrane to produce byproduct water.

The hydrogen fuel fluid stream supplied to a fuel cell anode may be, for example, substantially pure hydrogen, or a dilute hydrogen stream such as a reformate stream. Further, the anode exhaust stream containing unreacted hydrogen, or a portion thereof, may be recirculated back to the fuel cell, depending upon a measured concentration of unreacted hydrogen contained in the exhaust stream. It is known to provide hydrogen sensors operably associated with a fuel cell exhaust stream for measuring a concentration of hydrogen in the exhaust stream. Further, the concentration of hydrogen within the exhaust stream may be used as an indicator of the fuel cell performance and operating efficiency. For example, if there is an excessive amount of hydrogen in the fuel stream exhausted from the fuel cell, it may indicate poor operating efficiency.

However, fuel cell exhaust gasses consist of nitrogen, trace hydrogen, liquid water and water vapor at a temperature between 60° C. and 80° C. (140° F. and 176° F.) with nearly 100% relative humidity. This high absolute humidity generates condensate inside the hydrogen sensor, which may result in temporary or permanent incorrect hydrogen concentration readings. Additionally, chemical hydrogen sensors, such as those used in current fuel cell vehicles, generate water vapor by themselves due to a reaction of free hydrogen with oxygen on the surface of the sensor while detecting the hydrogen concentration.

Available hydrogen concentration sensors are designed for ambient application and usage in low humidity environments. It is known that use of available sensors in high humidity environments where condensation and water drops may occur adversely impacts the lifetime and reliability of the sensor. The combination of high temperature and high humidity within the sensor assembly may lead to corrosion or degradation of the sensor or components and wiring thereof, requiring premature and costly replacement of the sensor. Moreover, it has been determined that condensed water inside the hydrogen sensor is a primary reason for diminished reliability and durability of the sensor.

Use of available hydrogen concentration sensors for fuel cell exhaust gas applications does not meet automotive requirements for durability, reliability and cost. Presently, a primary method of addressing the drawbacks of current sensor technology is to provide specially designed sensors that deter corrosion of the sensor. These exhaust sensors, for example, require coated contacts, making the system more expensive. It is therefore desirable to provide an ambient hydrogen sensor that does not corrode, eliminating a cost intensive measure of frequent exchanges or replacements of the hydrogen sensor after a relatively limited number of operational hours. The high frequency of the sensor exchange rate impacts a vehicle's reliability, removes it from service frequently for sensor replacement, and increases the servicing or lifetime costs of the vehicle.

There is a continuing need for a cost effective, long lifetime hydrogen concentration sensor assembly that militates against water vapor condensation and liquid water inside the sensor housing.

SUMMARY OF THE INVENTION

Concordant and consistent with the present invention, a hydrogen sensor assembly that militates against water vapor condensation inside a hydrogen sensor to thereby minimize degradation of the hydrogen sensor and maximize the reliability thereof has surprisingly been discovered.

In one embodiment, a hydrogen sensor assembly comprises a sensor disposed within a slotted sleeve; and an arcuate shaped sensor housing disposed radially outwardly from the sleeve, wherein the sleeve forms an internal inner perimeter of the spiral housing, and wherein the sensor housing includes a first opening to facilitate a fluid communication between the sensor assembly and a fluid stream.

In another embodiment, a hydrogen sensor assembly comprises a sensor disposed within a sleeve; and a spiral shaped sensor housing surrounding the sensor within the sleeve and having a first opening to facilitate a fluid communication between the sensor assembly and a fluid stream, wherein the spiral shaped sensor housing is configured to create a centrifugal force which separates liquid water from the fluid stream as the fluid stream flows through the housing.

In a further embodiment, a method for measuring the hydrogen concentration in a fuel cell exhaust stream comprises the steps of disposing a hydrogen sensor assembly within the exhaust stream of a fuel cell, wherein said hydrogen sensor assembly comprises a sensor disposed within a sleeve and a spiral shaped sensor housing surrounding the sensor within the sleeve; providing fluid communication between the exhaust stream and the hydrogen sensor assembly; the spiral shaped sensor housing creating a centrifugal force on a fluid stream flowing through the spiral shaped sensor housing and around the hydrogen sensor; and the sensor measuring the hydrogen concentration of the fluid stream.

BRIEF DESCRIPTION OF THE DRAWINGS

The above, as well as other advantages of the present invention, will become readily apparent to those skilled in the art from the following detailed description of the preferred embodiment when considered in the light of the accompanying drawing.

FIG. 1 is a schematic elevational view of a hydrogen sensor assembly according to an embodiment of the present invention; and FIG. 2 is a schematic plan view of FIG. 1.

DETAILED DESCRIPTION OF EXEMPLARY EMBODIMENTS OF THE INVENTION

The following detailed description and appended drawings describe and illustrate various embodiments of the invention. The description and drawings serve to enable one skilled in the art to make and use the invention, and are not intended to limit the scope of the invention in any manner.

A sensor assembly 10 is shown in FIGS. 1 and 2. The sensor assembly 10 includes a hydrogen sensor 12 within a sensor sleeve 14. In one embodiment, the sensor sleeve 14 includes slots 16. The sensor sleeve 14 forms an internal inner perimeter 22 of a sensor housing 18. In the embodiment shown, the sensor housing 18 is substantially spiral shaped and surrounds the sensor sleeve 14. The shape of the sensor housing 18 applies a centrifugal force effect upon a fluid flowing therein as described below. The shape of the housing 18 may be in any form so long as a centrifugal force effect is maintained upon the fluid stream 26. In one embodiment, the fluid stream 26 is the exhaust gas stream of a fuel cell. The sensor assembly 10 is located adjacent a fluid plenum 24 and in fluid communication therewith. In another embodiment, the fluid plenum 24 is an exhaust gas plenum 24. The fluid stream 26 flows through the fluid plenum 24, and includes trace levels of free hydrogen ($H_2$) and free oxygen ($O_2$), nitrogen ($N_2$), water vapor, water drops and various contaminants. The fluid stream 26 within the fluid plenum 24 typically flows at a temperature between 60° C. and 80° C. (140° F. and 176° F.) with nearly 100% relative humidity. As a result, a very small temperature drop within the fluid plenum 24 or within the sensor housing 18 will result in condensation of water 28 within the fuel cell fluid stream 26.

Within the sleeve 14 of the hydrogen sensor 12, various electronics are packaged, depending upon the type of the sensor being used. The electronics are electrically coupled to a sensing element (not shown). It is understood that the sensing element may be any type of sensing element. However, for purposes of illustration, the sensing element is a hydrogen sensor. It is further understood that the electronics are adapted to convert a signal received from the sensing element into data representing a hydrogen concentration level. Sensing of the hydrogen concentration level of the fuel cell exhaust stream is accomplished by providing slots 16 around the perimeter of the sleeve 14. It is further understood that the dimensions of the slots 16 are dependent on the sensing element of the sensor 12. The sleeve 14 with slots 16 forms the internal inner perimeter 22 of the spiral sensor housing 18.

The sensor housing 18 is disposed within the fluid plenum 24 and in fluid communication with the fluid stream 26. The fluid stream 26 flows from a first opening 24' of the sensor housing 18, through the sensor housing 18, exiting through a second opening 24" into the fluid plenum 24. As stated above, the sensor housing 18 is spiral shaped and has an internal outer perimeter 20 and the internal inner perimeter 22 formed with the slotted sleeve 14.

In operation, the fluid stream 26 flows from the fluid plenum 24 into the first opening 24' of the sensor assembly 10. The fluid stream 26 is directed through the spiral shaped sensor housing 18. As the fluid stream 26 enters the housing 18, water vapor forms condensation 28 within the housing 18. The spiral shape of the housing 18 spins the fluid about the spiral internal outer and inner perimeters 20, 22 creating an asymmetric gas speed 30. The highest gas speed is at the internal outer perimeter 20 of the housing 18. The resulting centrifugal force upon the fluid stream 26 causes the water 32 to flow to the internal outer perimeter 20. This results in a separation of the dry gas stream and the liquid water. The hydrogen sensor 12 measures a hydrogen concentration by detecting oxidation of free hydrogen, or by otherwise reacting hydrogen through the slotted sensor sleeve 14. Evacuation of the fluid stream 26 and water vapor condensation 32 produced within the sensor housing 18 is facilitated through a second opening 24" downstream of the housing 18 into the fluid plenum 24 to the ambient environment. Frequent replacement of the hydrogen sensor may therefore be avoided.

From the foregoing description, one ordinarily skilled in the art can easily ascertain the essential characteristics of this invention and, without departing from the spirit and scope thereof, make various changes and modifications to the invention to adapt it to various usages and conditions.

What is claimed is:

1. A hydrogen sensor assembly comprising:
   a sensor disposed within a slotted sleeve; and
   an arcuate shaped sensor housing disposed radially outwardly from the sleeve, wherein the sleeve forms an internal inner perimeter of the arcuate housing, and wherein the sensor housing includes a first opening to facilitate a fluid communication between the sensor assembly and a fluid stream.

2. The hydrogen sensor assembly of claim 1, further comprising a second opening in the sensor housing to facilitate a fluid communication between the sensor assembly and the environment.

3. The hydrogen sensor assembly of claim 1, wherein the fluid stream is an exhaust stream of a fuel cell.

4. The hydrogen sensor assembly of claim 2, wherein the sensor housing is configured to create a centrifugal force on the fluid stream as the fluid stream flows from the first opening to the second opening.

5. The hydrogen sensor assembly of claim 4, wherein the sensor is configured to sense a concentration of hydrogen within the fluid stream as the fluid stream flows from the first opening to the second opening.

6. The hydrogen sensor assembly of claim 1, wherein the sensor housing is spiral shaped.

7. A hydrogen sensor assembly comprising:
   a sensor disposed within a sleeve; and
   a spiral shaped sensor housing surrounding the sensor within the sleeve and having a first opening to facilitate a fluid communication between the sensor assembly and a fluid stream, wherein the spiral shaped sensor housing is configured to create a centrifugal force which separates liquid water from the fluid stream as the fluid stream flows through the housing.

8. The hydrogen sensor of claim 7, wherein the sleeve forms an internal inner perimeter of the spiral shaped sensor housing.

9. The hydrogen sensor assembly of claim 8, wherein the sleeve further comprises slots formed therein configured to facilitate measuring a concentration of hydrogen within the fluid stream by the sensor as the fluid stream flows from the first opening through the sensor housing.

10. The hydrogen sensor assembly of claim 7, further comprising a second opening in the sensor housing to facilitate a fluid communication between the sensor assembly and the environment.

11. The hydrogen sensor assembly of claim 7, wherein the fluid stream is an exhaust stream of a fuel cell.

12. A method for measuring the hydrogen concentration in a fuel cell exhaust stream comprising the steps of:
- disposing a hydrogen sensor assembly within the exhaust stream of a fuel cell, wherein said hydrogen sensor assembly comprises a sensor disposed within a sleeve and a spiral shaped sensor housing surrounding the sensor within the sleeve;
- providing fluid communication between the exhaust stream and the hydrogen sensor assembly;
- the spiral shaped sensor housing creating a centrifugal force on a fluid stream flowing through the spiral shaped sensor housing and around the hydrogen sensor; and
- the sensor measuring the hydrogen concentration of the fluid stream.

13. The hydrogen sensor of claim 12, wherein the sensor sleeve forms an internal inner perimeter of the spiral shaped sensor housing.

14. The hydrogen sensor assembly of claim 13, wherein the sensor sleeve further comprises slots formed therein for exposing the sensor to the fluid stream during the step of measuring a hydrogen concentration of the fluid stream.

* * * * *